(12) United States Patent
Sharp et al.

(10) Patent No.: US 11,737,648 B2
(45) Date of Patent: Aug. 29, 2023

(54) CORDLESS DISPOSABLE ENDOSCOPE

(71) Applicant: Integrated Endoscopy, Inc., Irvine, CA (US)

(72) Inventors: Andrew Ryan Sharp, Irvine, CA (US); Siddharth Balvantrai Desai, Mission Viejo, CA (US)

(73) Assignee: INTEGRATED ENDOSCOPY, INC., Irvine, CA (US)

( * ) Notice: Subject to any disclaimer, the term of this patent is extended or adjusted under 35 U.S.C. 154(b) by 52 days.

(21) Appl. No.: 16/812,681

(22) Filed: Mar. 9, 2020

(65) Prior Publication Data

US 2020/0305688 A1 Oct. 1, 2020

Related U.S. Application Data

(60) Provisional application No. 62/816,758, filed on Mar. 11, 2019.

(51) Int. Cl.
*A61B 1/00* (2006.01)
*A61B 1/005* (2006.01)
(Continued)

(52) U.S. Cl.
CPC ........ *A61B 1/00062* (2013.01); *A61B 1/0011* (2013.01); *A61B 1/00029* (2013.01);
(Continued)

(58) Field of Classification Search
CPC ............ A61B 1/00103; A61B 1/00105; A61B 1/00062; A61B 1/00029; A61B 1/00066;
(Continued)

(56) References Cited

U.S. PATENT DOCUMENTS

D250,084 S 10/1978 Kirschensteiner
D292,227 S 10/1987 Rudelick
(Continued)

FOREIGN PATENT DOCUMENTS

CN 305308624 8/2019
EP 2 623 018 A 8/2013
KR 300843231.0000 3/2016

OTHER PUBLICATIONS

"Acupress Pen Stand Holder". Found online Dec. 29, 2020 at amazon.com. Reference dated Apr. 26, 2016. Retrieved from https://www.amazon.com/Acupress-Holder-Compatible-Intuos-CTL680/dp/B01ESYEWWU. (Year: 2016).
(Continued)

*Primary Examiner* — Aaron B Fairchild
*Assistant Examiner* — Stephen Floyd London
(74) *Attorney, Agent, or Firm* — Knobbe, Martens, Olson & Bear LLP

(57) ABSTRACT

A cordless endoscope assembly includes a housing, an endoscope tube and an eyepiece. Electronics are housed in the housing and operable to operate one or more light sources in the endoscope, the electronics including one or more batteries and a printed circuit board. The housing includes a connector configured to removably couple with a cannula connector of a cannula when the endoscope tube is inserted through the cannula. The cordless endoscope is a disposable single use endoscope that can optionally be sterilized with an ethylene oxide (EtO) sterilization process.

19 Claims, 12 Drawing Sheets

(51) Int. Cl.
*A61B 1/04* (2006.01)
*A61B 1/06* (2006.01)
*A61L 2/20* (2006.01)

(52) U.S. Cl.
CPC ........ *A61B 1/0052* (2013.01); *A61B 1/00066* (2013.01); *A61B 1/00103* (2013.01); *A61B 1/00105* (2013.01); *A61B 1/00112* (2013.01); *A61B 1/042* (2013.01); *A61B 1/0661* (2013.01); *A61L 2/206* (2013.01); *A61L 2202/24* (2013.01)

(58) Field of Classification Search
CPC . A61B 1/0011; A61B 1/00112; A61B 1/0052; A61B 1/042; A61B 1/0661; A61B 1/317; A61B 1/0669; A61B 1/0684; A61B 1/00135; A61B 1/00154; A61B 1/00128; A61B 1/00032; A61B 1/00034; A61B 1/00042; A61B 1/00101; A61B 1/00108; A61B 1/0014; A61B 1/00142; A61B 1/00195; A61B 1/00197; A61B 1/227; A61B 1/2275; A61L 2/206; A61L 2202/24

See application file for complete search history.

(56) References Cited

U.S. PATENT DOCUMENTS

| | | | |
|---|---|---|---|
| 4,782,819 A * | 11/1988 | Adair | A61B 1/00128 606/10 |
| D325,857 S | 5/1992 | Hasegawa | |
| D349,559 S | 8/1994 | Vanderhoef | |
| D350,194 S | 8/1994 | Marino | |
| D352,780 S | 11/1994 | Glaeser | |
| D352,872 S | 11/1994 | Crockett | |
| D353,888 S | 12/1994 | Raines | |
| D396,624 S | 8/1998 | Basilius | |
| 5,797,836 A | 8/1998 | Lucey | |
| D409,563 S | 5/1999 | Haase | |
| D436,118 S | 1/2001 | London | |
| D436,165 S | 1/2001 | Donaldson | |
| D436,819 S | 1/2001 | Liu | |
| D437,539 S | 2/2001 | Kilmer | |
| D441,834 S | 5/2001 | McGrath | |
| D453,376 S | 2/2002 | McMahon | |
| D454,951 S | 3/2002 | Bon | |
| D466,213 S | 11/2002 | Snitkin | |
| D471,578 S | 3/2003 | Okuley | |
| D476,542 S | 7/2003 | Chunn | |
| D478,986 S | 8/2003 | Johnston | |
| D485,148 S | 1/2004 | Chen | |
| D485,737 S | 1/2004 | Schaub | |
| D486,370 S | 2/2004 | Chen | |
| D486,713 S | 2/2004 | Lai | |
| D487,219 S | 3/2004 | Chudy | |
| D487,384 S | 3/2004 | Neitzel | |
| D488,040 S | 4/2004 | Chen | |
| D488,041 S | 4/2004 | Chen | |
| D488,042 S | 4/2004 | Enck | |
| D493,085 S | 7/2004 | Copeland, II | |
| 6,761,684 B1 | 7/2004 | Speier | |
| D497,786 S | 11/2004 | Concari | |
| D498,400 S | 11/2004 | Wu | |
| D508,458 S | 8/2005 | Solland | |
| D508,835 S | 8/2005 | Schiller | |
| D508,836 S | 8/2005 | Schiller | |
| D509,119 S | 9/2005 | Schiller | |
| D513,160 S | 12/2005 | DeBoer | |
| D513,690 S | 1/2006 | Etter | |
| D514,413 S | 2/2006 | Cuenca | |
| D515,393 S | 2/2006 | Lin | |
| D515,895 S | 2/2006 | Chen | |
| D516,889 S | 3/2006 | Aglassinger | |
| D516,890 S | 3/2006 | Huang | |
| D521,927 S | 5/2006 | Franck | |
| D524,133 S | 7/2006 | Wu | |
| D524,282 S | 7/2006 | Beasley | |
| D524,625 S | 7/2006 | Wu | |
| D527,600 S | 9/2006 | Stratford | |
| D530,818 S | 10/2006 | Lin | |
| D531,000 S | 10/2006 | Meyers | |
| D531,872 S | 11/2006 | Aglassinger | |
| D531,873 S | 11/2006 | Liu | |
| D532,666 S | 11/2006 | Chi | |
| D542,618 S | 5/2007 | Miura | |
| D545,427 S | 6/2007 | Gibson | |
| D545,428 S | 6/2007 | Stammberger | |
| D551,762 S | 9/2007 | Root | |
| D565,920 S | 4/2008 | Bagley | |
| D589,515 S | 3/2009 | Brunner | |
| D597,392 S | 8/2009 | Meyers | |
| D599,884 S | 9/2009 | Zore | |
| D602,858 S | 10/2009 | Ellis | |
| D604,844 S | 11/2009 | Summerer | |
| D605,487 S | 12/2009 | Aglassinger | |
| D605,488 S | 12/2009 | Aglassinger | |
| D605,489 S | 12/2009 | Aglassinger | |
| D606,827 S | 12/2009 | Fritz | |
| D610,679 S | 2/2010 | Nakagawa | |
| D625,058 S | 10/2010 | Kovach | |
| D627,718 S | 11/2010 | Houghton | |
| D628,290 S | 11/2010 | Romero | |
| D653,206 S | 1/2012 | Heine | |
| D657,646 S | 4/2012 | Schoch | |
| D658,026 S | 4/2012 | Dale | |
| D658,741 S | 5/2012 | Romero | |
| D670,389 S | 11/2012 | Chen | |
| D676,377 S | 2/2013 | Nokuo | |
| D677,741 S | 3/2013 | Wilson | |
| D677,830 S | 3/2013 | Daniels | |
| D678,980 S | 3/2013 | Nies | |
| D702,319 S | 4/2014 | Mammen | |
| D702,648 S | 4/2014 | Ichio | |
| D702,649 S | 4/2014 | Ichio | |
| D706,980 S | 6/2014 | Tasar | |
| D713,933 S | 9/2014 | Mammen | |
| D713,934 S | 9/2014 | Mammen | |
| D714,423 S | 9/2014 | Mammen | |
| D714,908 S | 10/2014 | Mammen | |
| D719,651 S | 12/2014 | Hoffmann | |
| D735,133 S | 7/2015 | Reishus | |
| D736,350 S | 8/2015 | Cheng | |
| D736,887 S | 8/2015 | Schwarz | |
| D747,441 S | 1/2016 | Naslund | |
| D751,196 S | 3/2016 | Wapler | |
| D753,823 S | 4/2016 | Hayamizu | |
| D762,571 S | 8/2016 | Lee | |
| D771,243 S | 11/2016 | DiMino | |
| D798,686 S | 10/2017 | Barakat | |
| D799,036 S | 10/2017 | Osada | |
| D810,679 S | 2/2018 | Patton | |
| D813,806 S | 3/2018 | Ito | |
| D824,487 S | 7/2018 | Montoya | |
| D824,488 S | 7/2018 | Montoya | |
| D824,489 S | 7/2018 | Montoya | |
| D824,490 S | 7/2018 | Montoya | |
| D824,491 S | 7/2018 | Montoya | |
| D824,626 S | 7/2018 | Vosbikian | |
| D826,025 S | 8/2018 | Harrington | |
| D831,212 S | 10/2018 | Clifford | |
| D831,819 S | 10/2018 | Genender | |
| D837,215 S | 1/2019 | Memke | |
| D838,155 S | 1/2019 | Chen | |
| D838,301 S | 1/2019 | Prikler | |
| D840,032 S | 2/2019 | Clifford | |
| D841,160 S | 2/2019 | Cranfield | |
| D841,788 S | 2/2019 | Gough | |
| D842,465 S | 3/2019 | Osada | |
| D844,405 S | 4/2019 | Shen | |
| D851,644 S | 6/2019 | Memke | |
| D852,357 S | 6/2019 | Osada | |
| D852,358 S | 6/2019 | Matuschek | |
| D860,441 S | 9/2019 | Spycher | |

(56) References Cited

U.S. PATENT DOCUMENTS

| | | | |
|---|---|---|---|
| D864,857 S | 10/2019 | Clark | |
| D865,289 S | 10/2019 | Huang | |
| D869,927 S | 12/2019 | Waldron | |
| D873,413 S | 1/2020 | Ohno | |
| D873,957 S | 1/2020 | Daudish | |
| D874,643 S | 2/2020 | Genender | |
| D886,558 S | 6/2020 | Koenigsberger | |
| D886,561 S | 6/2020 | Lundbaeck | |
| D890,088 S | 7/2020 | Machida | |
| D892,907 S | 8/2020 | Chan | |
| D893,709 S | 8/2020 | Girod | |
| D895,542 S | 9/2020 | Bell | |
| D895,757 S | 9/2020 | Leis | |
| D896,364 S | 9/2020 | Genender | |
| D898,533 S | 10/2020 | Lundbaeck | |
| D898,910 S | 10/2020 | Hansen | |
| D900,737 S | 11/2020 | Hsu | |
| D902,150 S | 11/2020 | Sun | |
| D902,401 S | 11/2020 | Ohno | |
| D904,608 S | 12/2020 | Attinger | |
| D905,241 S | 12/2020 | Ohno | |
| D905,520 S | 12/2020 | Huang | |
| D906,076 S | 12/2020 | James | |
| D907,456 S | 1/2021 | Diaz | |
| D908,961 S | 1/2021 | Yang | |
| D911,400 S | 2/2021 | Tsai | |
| D918,088 S | 5/2021 | Fumex | |
| 2002/0095068 A1* | 7/2002 | Lubowski | A61B 1/3132 600/156 |
| 2003/0043042 A1 | 3/2003 | Moores, Jr. | |
| 2003/0146735 A1 | 8/2003 | Barbeau | |
| 2004/0199052 A1 | 10/2004 | Banik | |
| 2006/0041193 A1 | 2/2006 | Wright | |
| 2006/0100483 A1* | 5/2006 | Sundet | A61B 1/267 600/156 |
| 2006/0229495 A1* | 10/2006 | Frith | A61B 1/00126 600/112 |
| 2006/0262525 A1 | 11/2006 | Barbeau | |
| 2008/0041394 A1 | 2/2008 | Swann | |
| 2008/0058595 A1* | 3/2008 | Snoke | A61B 1/00135 600/114 |
| 2008/0086033 A1 | 4/2008 | Mihalca | |
| 2008/0139881 A1 | 6/2008 | Cover | |
| 2008/0195128 A1* | 8/2008 | Orbay | A61B 1/00105 600/183 |
| 2008/0262654 A1* | 10/2008 | Omori | A61B 34/70 700/245 |
| 2009/0057544 A1 | 3/2009 | Brodie | |
| 2009/0303619 A1 | 12/2009 | Iwasaki | |
| 2011/0092772 A1 | 4/2011 | Weber | |
| 2011/0263941 A1 | 10/2011 | Wright et al. | |
| 2011/0306834 A1 | 12/2011 | Schrader | |
| 2011/0317403 A1 | 12/2011 | Fournier | |
| 2012/0230017 A1 | 9/2012 | Duffy | |
| 2013/0331730 A1 | 12/2013 | Fenech | |
| 2014/0005478 A1* | 1/2014 | Kennedy, II | A61B 10/04 600/114 |
| 2014/0221749 A1* | 8/2014 | Grant | A61B 1/126 600/109 |
| 2015/0366560 A1* | 12/2015 | Chen | A61B 90/92 227/176.1 |
| 2016/0316998 A1* | 11/2016 | Lombardi | A61B 1/307 |
| 2017/0035276 A1 | 2/2017 | Lombardi | |
| 2017/0187212 A1 | 6/2017 | Hemesath | |
| 2019/0133432 A1* | 5/2019 | Tsai | A61B 1/0684 |
| 2019/0207402 A1 | 7/2019 | Renken | |
| 2019/0374095 A1* | 12/2019 | Lord | A61B 1/053 |
| 2020/0205644 A1* | 7/2020 | Nakajima | A61B 1/00096 |
| 2020/0315444 A1* | 10/2020 | Ramanujam | A61B 1/00016 |

OTHER PUBLICATIONS

"Charging Dock and Base for Knuckle Lights Advanced". Found online Dec. 30, 2020 at knucklelights.com. Reference dated Jun. 25, 2019. Retrieved from https://knucklelights.com/products/charging-base. (Year: 2020).

"Kebor Hair Clippers". Found online Dec. 30, 2020 at amazon.com. Reference dated Apr. 19, 2019. Retrieved from https://us.amazon.com/Kebor-Clippers-Electric-Rechargeable-Lithium-ion/dp/B079GS6CDH. (Year: 2019).

"Revolabs Charger Base". Found online Dec. 30, 2020 at bhphotovideo.com. Reference dated Aug. 15, 2016. Retrieved from https://www.bhphotovideo.com/c/product/894848-REG/revolabs_02hddualchg11_charger_base_for_hd.html/qa. (Year: 2016).

"PULUZ Charging Dock". Found online Jan. 21, 2021 at miabyron.blogspot.com. Reference dated Jun. 3, 2019. Retrieved from https://miabyron.blogspot.com/2019/06/puluz-pu381-charging-dock-base-charger.html. (Year: 2018).

"Nikon Battery Charger Set". Found online Jan. 21, 2021 at newbecca.com. Reference dated Feb. 9, 2018. Retrieved from https://tineye.com/search/35fa9bc083a5e4b862a861548dc19c9785657fc7?sort=crawl_date&order=asc&page=1. (Year: 2018).

PCT International Search Report and Written Opinion dated May 28, 2020 regarding International Application No. PCT/US2020/021490, 16 pages.

\* cited by examiner

CORDLESS DISPOSABLE ENDOSCOPE

CROSS-REFERENCE TO RELATED APPLICATION

Any and all applications for which a foreign or domestic priority claim is identified in the Application Data Sheet as filed with the present application are hereby incorporated by reference under 37 CFR 1.57.

BACKGROUND

Field

Aspects of the present disclosure are directed to endoscopes, arthroscopes, and other medical imaging devices, and more particularly to cordless disposable endoscopes or arthroscopes that can be used, for example, in arthroscopic surgical procedures.

Description of the Related Art

Endoscopes generally include an elongate tubular structure that includes optics for imaging. Endoscopes may additionally be configured to provide illumination. Since endoscopes can provide images of within the patient's body, endoscopes are useful diagnostic and/or surgical tools. Endoscopes are widely used in medical procedures. In operation, the endoscope is inserted through an access cannula that has been inserted into the patient (e.g., via an incision), and the endoscope is locked to the cannula via the cannula's locking mechanism that couples to a portion of the endoscope. Various cannula manufacturers provided cannulas with different locking mechanisms, requiring different endoscopes to mate with the particular cannula design. One drawback of conventional endoscopes is that conventional endoscopes are connected by a cable or cord to an external power supply to provide power to the illumination components in the endoscope, which can make their use cumbersome.

SUMMARY

The systems, methods and devices of this disclosure each have several innovative aspects, no single one of which is solely responsible for the desirable attributes disclosed herein.

In accordance with one aspect of the disclosure, a wireless endoscope is provided.

In accordance with another aspect of the disclosure, a disposable endoscope is provided.

In accordance with another aspect of the disclosure, a battery-powered disposable endoscope is provided.

In accordance with another aspect of the disclosure, a wireless disposable endoscope having a locking mechanism that can releasably lock onto a cannula for use in a minimally invasive surgical procedure (e.g., an arthroscopic procedure).

Various innovative aspects of the subject matter described in this disclosure can be implemented in the following embodiments:

In accordance with one aspect of the disclosure, a cordless endoscope assembly is provided. The endoscope assembly comprises a housing that defines an ergonomic handpiece sized to be held between a palm and one or more fingers of a user's hand, an endoscope tube that extends distally of the housing, and an eyepiece that extends proximally of the housing. Electronics are housed in the housing and configured to operate one or more light sources in the endoscope, the electronics comprising one or more batteries and a printed circuit board. The housing includes a connector configured to removably couple with a cannula connector of a cannula when the endoscope tube is inserted through the cannula.

In accordance with another aspect of the disclosure, a cordless endoscope kit is provided. The kit comprises a rear housing portion and a plurality of front housing portions. Each front housing portion is coupleable to the rear housing portion to define a housing and ergonomic handpiece, each of the front housing portions having a different connector, each connector configured to couple to one of a plurality of different cannulas. The kit also comprises an endoscope tube that extends distally of the front housing portion and an eyepiece coupled to the rear housing portion. Electronics are housed in a cavity of the housing and configured to operate one or more light sources in the endoscope, the electronics comprising one or more batteries and a printed circuit board.

In accordance with another aspect of the disclosure, a method of manufacturing a cordless endoscope is provided. The method comprises forming or providing a rear housing portion and forming or providing a plurality of front housing portions. Each front housing portion is coupleable to the rear housing portion to define a housing and ergonomic handpiece. Each of the front housing portions have a different connector, each connector configured to couple to one of a plurality of different cannulas. The method also comprises selecting one of the plurality of front housing portions. The method also comprises disposing in a compartment between said one of the plurality of front housing portions and the rear housing portion electronics configured to operate one or more light sources in the endoscope, the electronics comprising a battery and a printed circuit board assembly (PCBA). The method also comprises coupling said one of the plurality of front housing portions to the rear housing portion to assemble the endoscope, an endoscope tube extending distally of the front housing portion and an eyepiece coupled to the rear housing portion, wherein the assembled endoscope is disposable as a single unit.

Details of one or more implementations of the subject matter described in this disclosure are set forth in the accompanying drawings and the description below. Although the examples provided in this disclosure are primarily described in terms of a medical imaging device, the concepts provided herein may apply to other types of imaging systems and devices. Other features, aspects, and advantages will become apparent from the description, the drawings and the claims. Note that the relative dimensions of the following figures may not be drawn to scale.

DETAILED DESCRIPTION OF VARIOUS EMBODIMENTS

Figure 8:
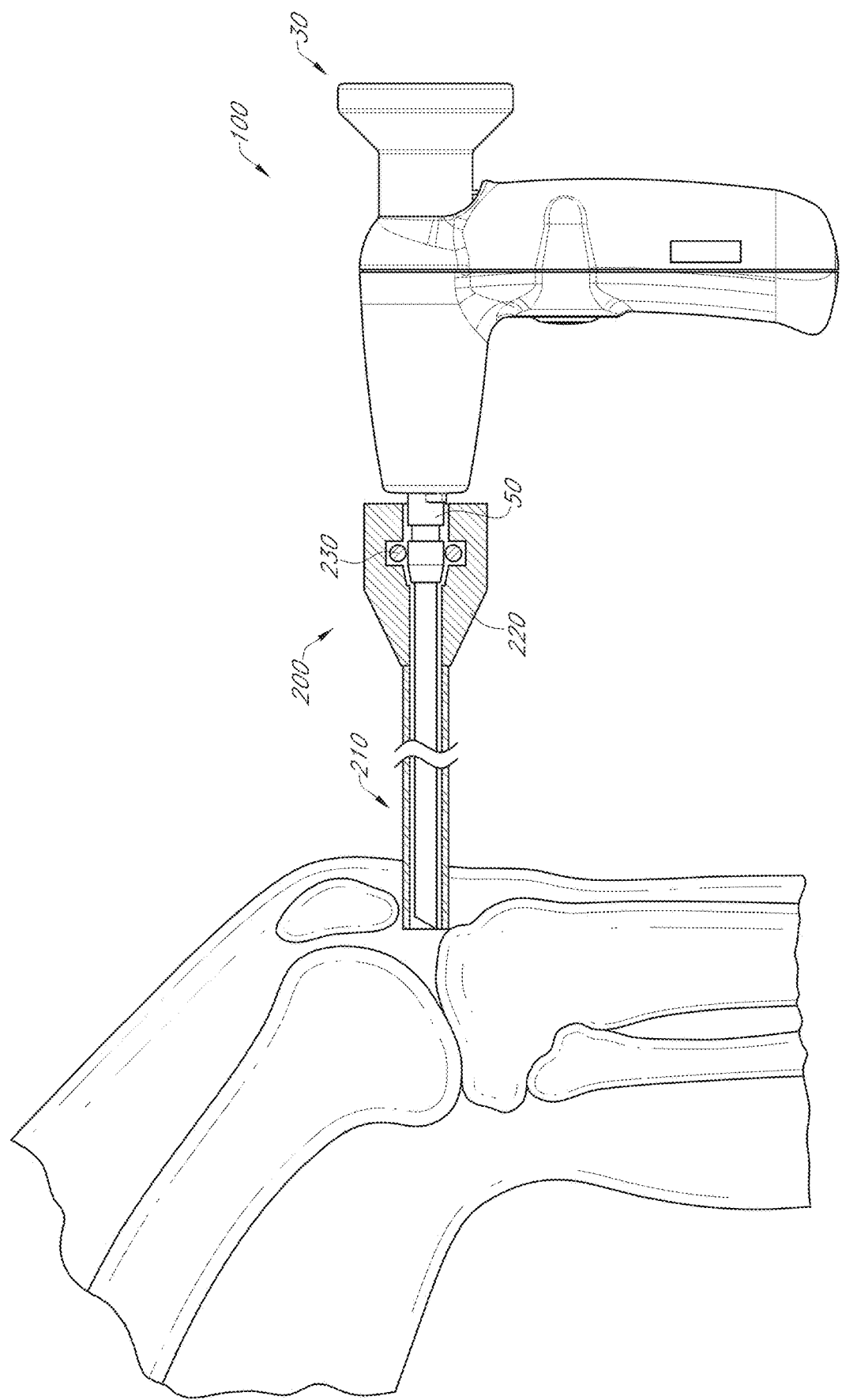
FIG. 8 is a schematic view of an endoscope inserted into a knee during a knee arthroscopic procedure.

Disclosed herein are endoscopes for viewing inside a cavity of a body. For illustrative purposes, FIGS. 1A-1D illustrates an endoscope 100 such as, for example, an arthroscope, that can be used to inspect one or more portions of a human body. For example, in one implementation, the endoscope 100 can be employed to inspect the interior of a knee K as shown in FIG. 8 (e.g., during an arthroscopic procedure on the knee K).

Figure 1A:
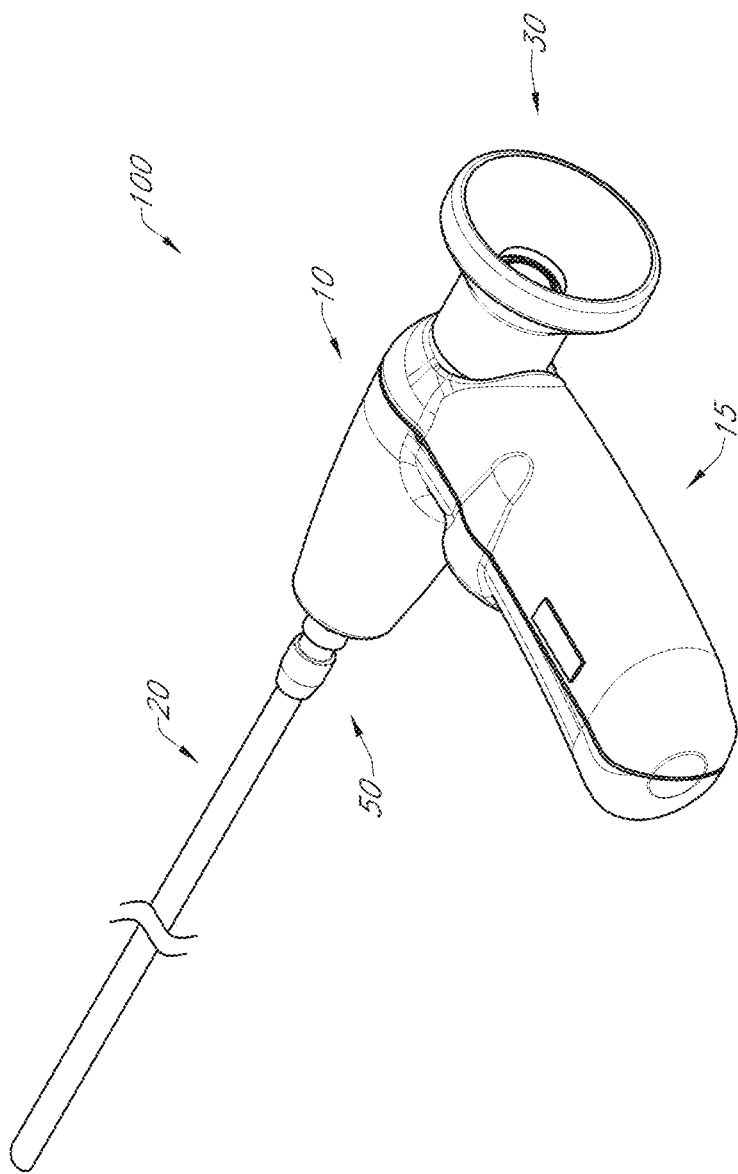
FIGS. 1A-1D illustrates a schematic perspective view, side view, enlarged side view and rear view of an endoscope, (e.g., an arthroscope).
Figure 1B:
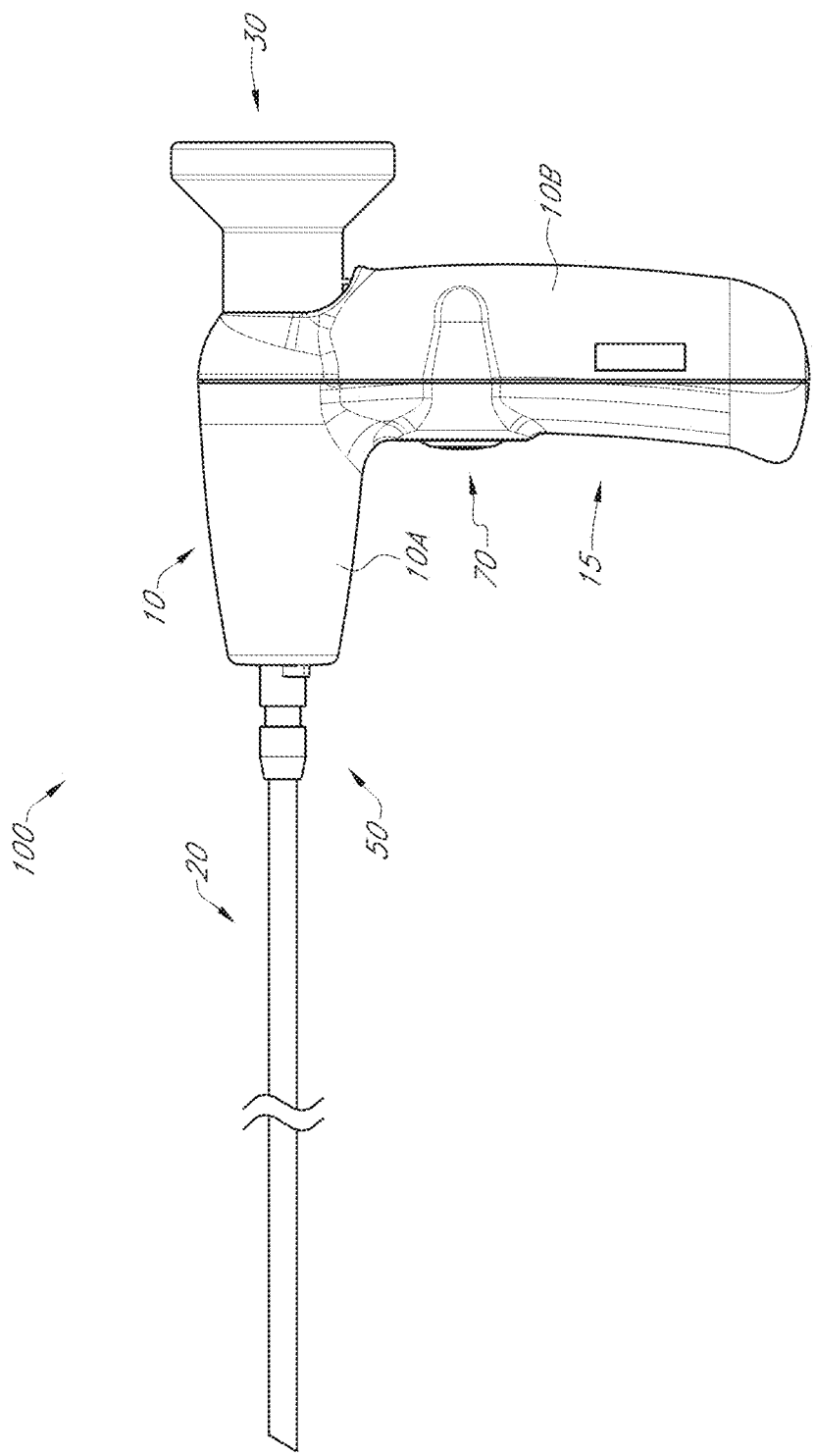
Figure 1C:
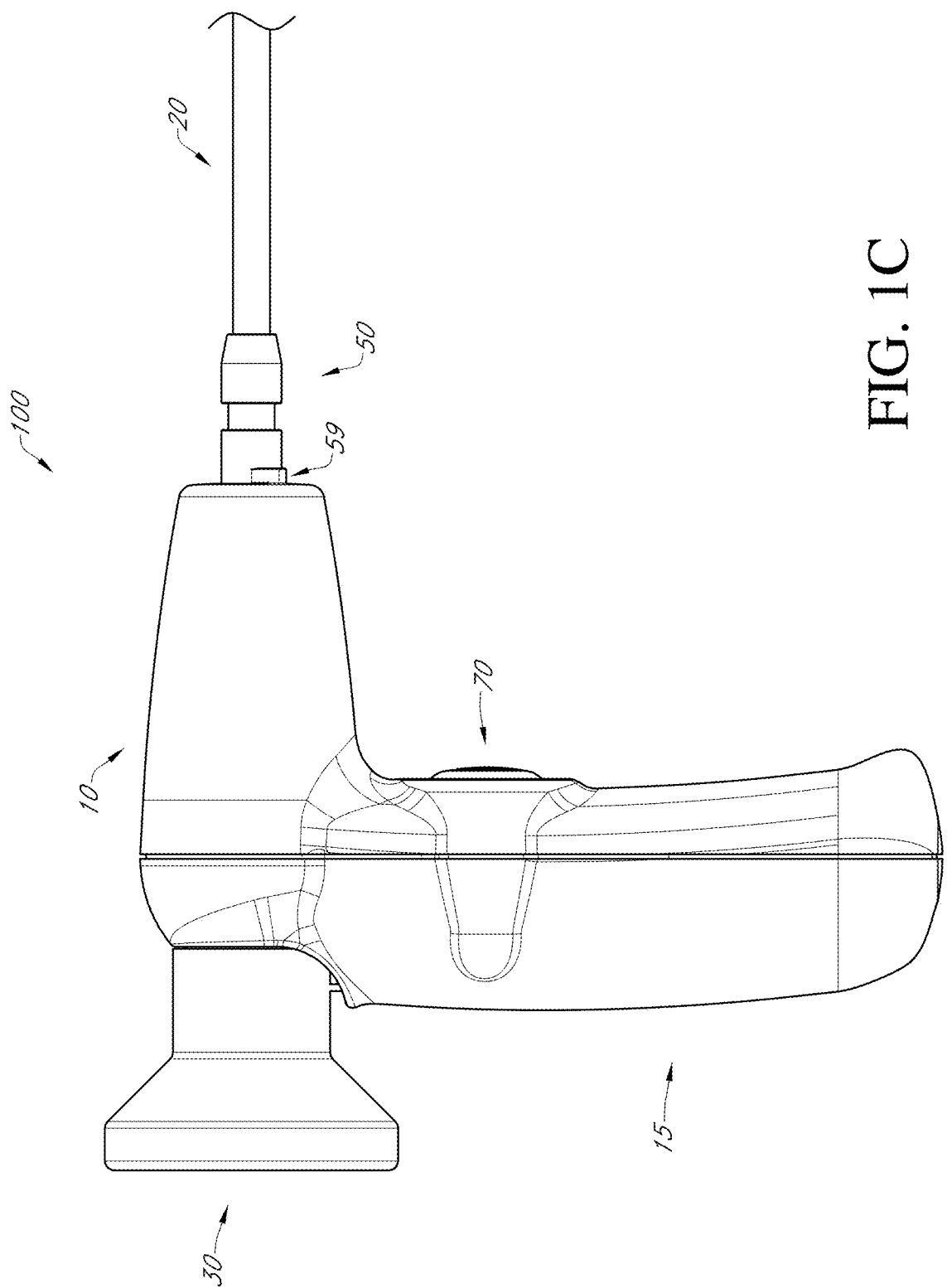
Figure 1D:
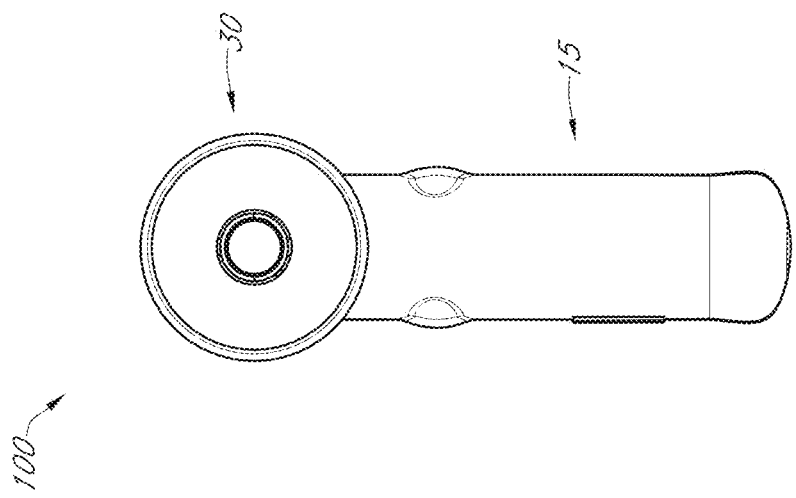
Figure 2:
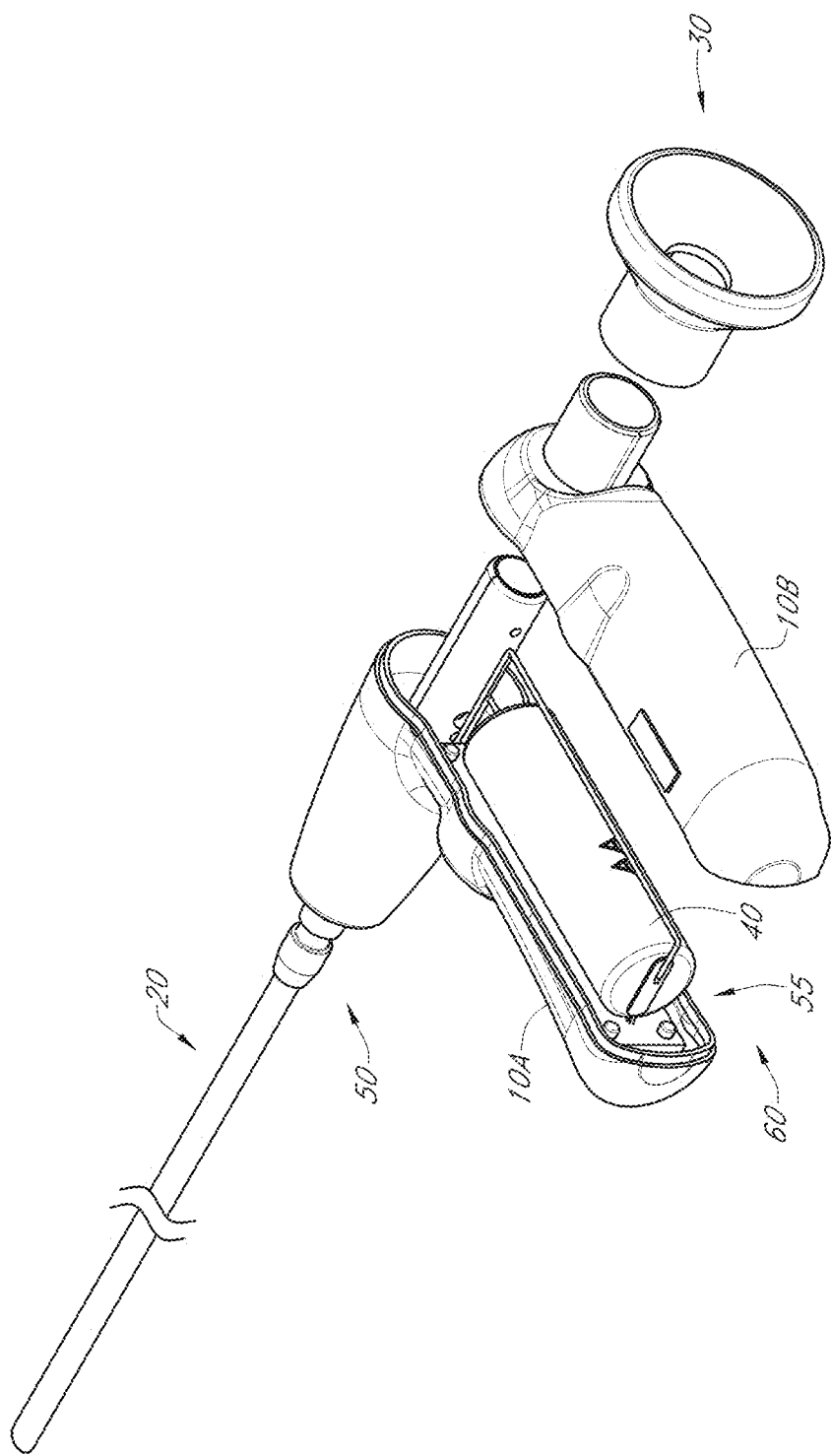
FIG. 2 illustrates a schematic exploded view of the endoscope (e.g., arthroscope) of FIG. 1A.

With reference to FIGS. 1A-2, the endoscope 100 (e.g., arthroscope) can have a housing 10, an endoscope tube or elongate member 20 (e.g., a rigid endoscope tube), and an eyepiece 30. The endoscope tube or elongate member 20 can optionally be made of stainless steel. In some implementations, the endoscope 100 can advantageously be disposable (e.g., single use).

The endoscope tube or elongate member 20 can have one or more (e.g., a plurality) of lenses disposed within an elongate tubular structure having proximal and distal ends. In some implementations, the lenses can be made of glass. In other implementations, the lenses can be made of plastic, such as polymethyl methacrylate (PMMA), Cyclic olefin copolymer (COC), or Cyclic olefin polymer (COP). The lenses can relay an image of features in the body located at the distal end of the endoscope 100 to the proximal end of the endoscope 100. In some embodiments, an imaging device (e.g., a camera or a detector such as a two-dimensional CCD or CMOS detector array) can be included at (e.g., attached to) the proximal end of the endoscope 100 to sense the relayed image. In some implementations, the eyepiece 30 or other optics may be used to view the image. In certain implementations, the endoscope 100 may additionally have a light source that is configured, sized, and positioned so as to be inserted into the body cavity to provide illumination therein. In some embodiments, for example, this light source is disposed at the distal end of the endoscope tube or elongate member 20. In some implementations, this light source comprises at least one solid state emitter, such as a light emitting diode (LED), located at the distal end of the endoscope.

In operation, light emitted from the light source illuminates various objects, surfaces, and features (e.g., walls) in the interior of the body cavity and is reflected off objects, surfaces, and features (e.g., walls) in the interior of the body cavity. A portion of the reflected light may be collected through an aperture at the distal end of the elongate member 20. This light may be directed along an optical path through the elongate member 20 formed by the plurality of lenses disposed in the elongate tubular structure so as to form an image of the objects, surfaces, features at the proximal end of the endoscope 100. The light collected may then be directed to the imaging device. Thus, an image of the object, surface, feature, etc. inside the body cavity can be viewed, for example, by the physician possibly on a display in communication with the detector.

Additional discussion of endoscopes is provided in U.S. patent application Ser. No. 11/099,435 (now U.S. Pat. No. 7,976,462) and U.S. patent application Ser. No. 14/567,879, each of which is incorporated by reference herein in its entirety and should be considered a part of this specification.

Advantageously, the endoscope 100 is wireless or cordless. That is, the endoscope 100 does not require the use of an external power source, and therefore does not need to have a power cord attached to it for operation. This makes the endoscope 100 easier and less cumbersome to handle and manipulate, for example during a surgical procedure, as the user (e.g., surgeon) is not encumbered by the power cord in the surgical field.

The housing 10 can have a front housing 10A and a rear housing 10B that couple to each other to define the housing 10. At least a portion of the housing 10 defines a handpiece 15 that can be grabbed by a user's hand to hold or orient the endoscope 100 as desired. Advantageously, the handpiece 15 is ergonomic, allowing the user (e.g., surgeon) to comfortably handle and manipulate (e.g., orient) the endoscope 100 during use. In one implementation, the handpiece 15 is sized to allow the rear housing 10B to be held in the palm of the user's hand while several fingers of the user's hand wrap around at least a portion of the front housing 10A. In one implementation, the housing 100 (e.g., the front housing 10A, the rear housing 10B) can be injection molded. In one implementation, the housing 100 (e.g., the front housing 10A, the rear housing 10B) can be made of a plastic material, such as Polycarbonate, Nylon, ABS (e.g. copolymer of acrylonitrile, butadiene and styrene), or other suitable polymers (e.g., thermoplastic polymers).

As discussed above, the endoscope 100 is advantageously wireless or cordless. The housing 10 can house one or more batteries 40 and electronics (e.g., a printed circuit board assembly or PCBA) 55 in a compartment 60 of the housing 10. The one or more batteries 40 and electronics 50 can power a light source (e.g., an LED light source in the endoscope 100) that can, for example, deliver light through the distal end of the endoscope tube 20, as further described herein.

The front housing 10A can include a connector 50 (e.g., at its distal end). The connector 50 can couple with a corresponding connector in a cannula 200 (See FIG. 9) that slides over and releasably couples with the connector 50, as described further below. The connector 50 can optionally have a groove or recess 52 (e.g., a circumferential groove) that receives a locking portion of the cannula 200 to lock the cannula 200 to the endoscope 100.

Figure 3:
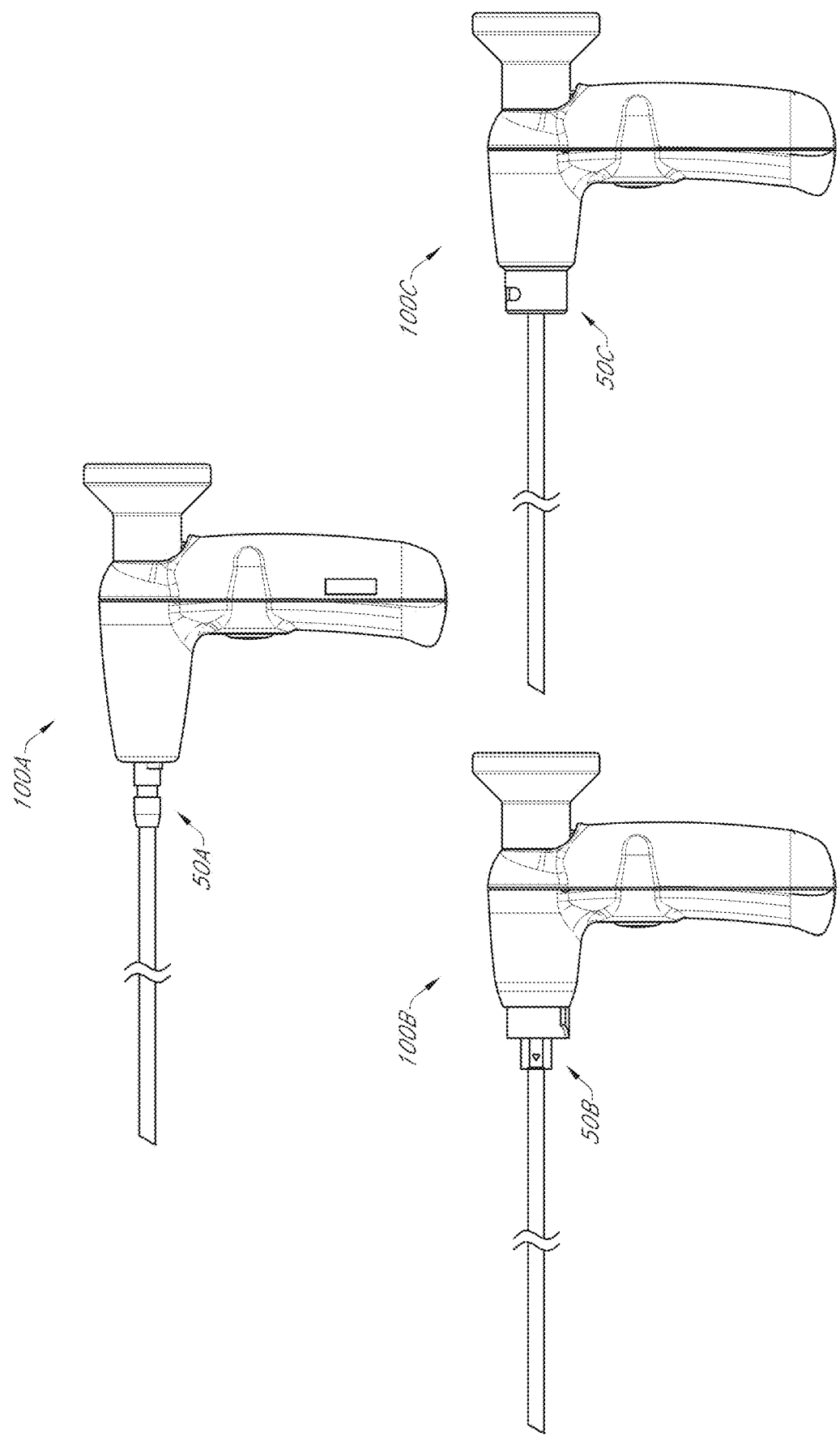
FIG. 3 illustrates a schematic side view of endoscopes shaped to releasably lock to different cannula designs.

FIG. 3 shows endoscopes 100A, 100B, 100C. The features of the endoscopes 100A, 100B, 100C are similar to features of the endoscope 100 in FIGS. 1A-2. Thus, references numerals used to designate the various components of the endoscopes 100A, 100B, 100C are identical to those used for identifying the corresponding components of the endoscope in FIGS. 1A-2, except that an "A", "B" or "C" is added to the numerical identifier. Therefore, the structure and description for the various features of the endoscope 100 in FIGS. 1A-2 are understood to also apply to the corresponding features of the endoscope 100A, 100B, 100C in FIG. 3, except as described below.

The endoscopes 100A, 100B, 100C differ in the shape and/or dimensions of the connector 50A, 50B, 50C (e.g., every other feature of the endoscopes 100A, 100B, 100C is similar, such as identical). Each connector 50A, 50B, 50C can have a different outer diameter, length and/or shape of the groove or recess 52A, 52B, 52C to allow each of the endoscopes 100A, 100B, 100C to couple to a cannula having a correspondingly shaped connector (e.g., such as connector 220 in FIG. 9). In particular, the connector 50A, 50B, 50C is sized and/or shaped so that a distal end of the cannula substantially aligns (e.g., within about 0.1 mm) with a distal end of the endoscope 100 (e.g., so that the endoscope 100 does not extend past the end of the cannula). Advantageously, the disposable, wireless endoscope 100A, 100B, 100C can interface with different manufacturers' cannulas, which have different locking mechanisms (e.g., different connectors 220). In one implementation, the user would order an endoscope for use with a particular manufacturer's cannula design for arthroscopic procedures, and the endoscope 100, 100A, 100B, 100C would be manufactured to correspond to the selected manufacturer's cannula (e.g., the front housing 10A would be selected to have the connector 50A, 50B, 50C that corresponds to the connector of the selected manufacturer's cannula).

Figure 4:
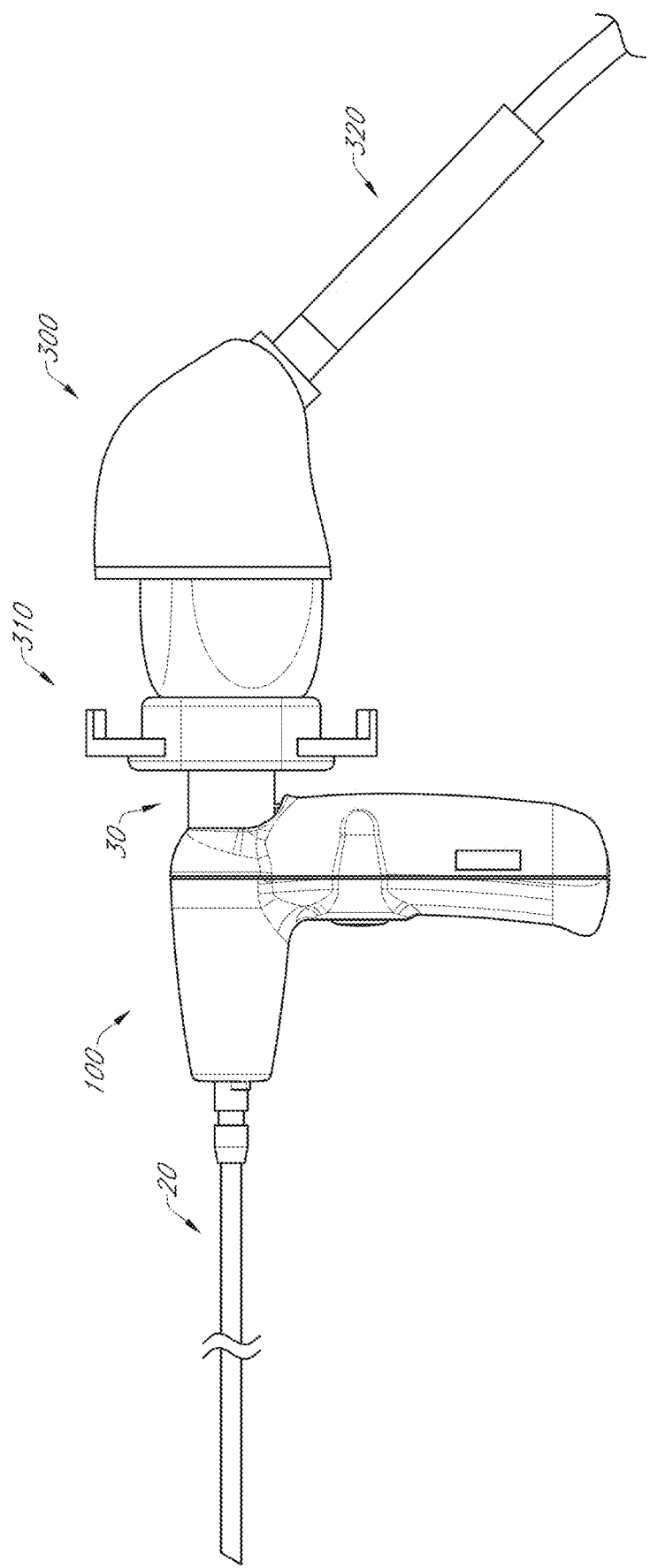
FIG. 4 illustrates a schematic side view of an endoscope coupled with a camera.

FIG. 4 shows the endoscope 100 coupled to an imaging device 300. The imaging device 300 can be a camera 300. The camera 300 can removably couple to the eyepiece 30 of the endoscope 100. Advantageously, the camera 300 has a coupler 310 that aligns with and removably couples to the eyepiece 30 of the endoscope 100. Advantageously, the endoscope 100 can be rotated about the axis of the endoscope tube 20 (e.g., by manually rotating the handpiece 15 about the axis of the endoscope tube 20) to provide the user (e.g., surgeon) with a different view (e.g., angular view) of the surgical site (e.g., the area inside the patient's body), such as due to the beveled end of the endoscope tube 20. Again, because the endoscope 100 is wireless (e.g., cordless), the user (e.g., surgeon) can easily rotate the endoscope 100 without the encumbrance of a power cord in the surgical field (e.g., the area outside the patient's body).

With continued reference to FIG. 4, the imaging device or camera 300 can transmit the images of various objects, surfaces, and features (e.g., walls) in the interior of the body cavity to a display device and/or a storage system over a wired connection (e.g., over a cable) 320. In other implementations, the imaging device 300 can transmit the images of various objects, surfaces, and features (e.g., walls) in the interior of the body cavity to a display device and/or a storage system over a wireless connection.

Figure 5:
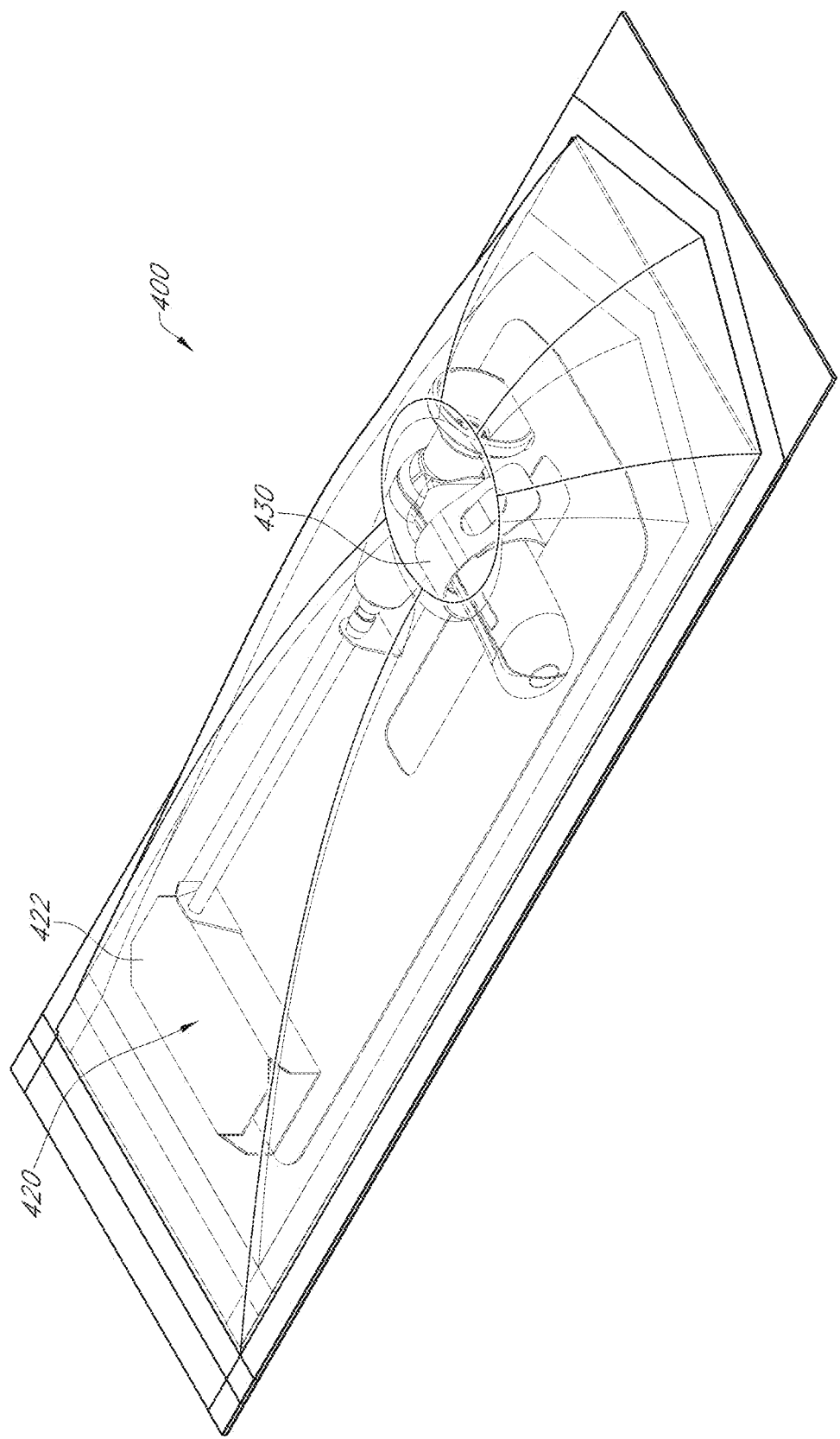
FIG. 5 illustrates a schematic perspective view of an endoscope in a package.

FIG. 5 shows an endoscope 100 in packaging 400. The endoscope 100 can be supported in a backer card 420. The backer card 420 can optionally have a frame portion 422 and a belt portion 430. The frame portion 422 can have an opening that receives and supports the end of the endoscope tube 20 in a suspended (e.g., cantilevered) manner. The belt portion 430 can wrap around the handpiece 15 of the endoscope 100. Accordingly, the backer card 420 supports the endoscope 100 in the packaging 400 to inhibit (e.g., prevent) inadvertent contact of the end of the endoscope 100 with a surface of the packaging 400.

As discussed above, certain implementations of the endoscope 100 may have a light source that is configured, sized, and positioned so as to be inserted into the body cavity to provide illumination therein. For example, this light source can be disposed at the distal end of the endoscope tube or elongate member 20. In some implementations, this light source can include at least one solid state emitter, such as a light emitting diode (LED), located at the distal end of the endoscope 100. The one or more batteries 40 in the endoscope 100 can provide power to the light source in the endoscope 100. This can advantageously make the endoscope 100 easier and less cumbersome to handle and manipulate, for example during a surgical procedure, as the user (e.g., surgeon) is not encumbered by a power cord in the surgical field, as discussed above.

In some implementations, the one or more batteries 40 in the endoscope 100 that power the light source can be one or more single use batteries 40. The single use batteries 40 can include alkaline batteries. For example, in some implementations, the light source can be powered by one or more AA batteries. As another example, the light source can be powered by one or more flat button cells. Employing one or more single use batteries has several advantages. For example, by employing batteries 40 to power the light source, the endoscope 100 need not be connected to an external power source (e.g., a power outlet) using a wired connection. This can make the endoscope easy and less cumbersome to handle/manipulate as discussed above.

Additionally, endoscopes utilizing such single use batteries as a power source are considered safe for sterilization using ethylene oxide (EtO). In another implementation, the endoscope 100 can be sterilized using an E-beam sterilization process. EtO sterilization is used to sterilize products that cannot withstand high temperature, such as, for example, products including electronic/opto-electronic components. During EtO sterilization, the product to be sterilized is exposed to air mixed with EtO gas. EtO is highly flammable and thus the product to be sterilized should not include components that can cause EtO to catch fire. Lithium ion batteries, which can be reused, can cause arcing during EtO sterilization which can cause EtO to catch fire. Single use batteries (e.g., alkaline AA batteries or flat button cell) can reduce to eliminate the risk of EtO catching fire during the sterilization process and thus are considered to be safe for EtO sterilization.

The one or more single use batteries 40 can be disposed in a compartment 60 of the housing 10. In some implementations, the compartment 60 can include a switch interface 70 disposed on the outside of the compartment 60. The switch interface 70 can engage an electronic switch (e.g., electronic switch 605 in FIG. 6) disposed inside the compartment 60 and electrically connected to the one or more single use batteries 40. The electronic switch can have different settings that are configured to change the amount of light output from the light source. For example, in some implementations, the electronic switch can have three modes: a first mode in which the light source emit light at a first optical power, a second mode in which the light source emit light at a second optical power different from the first optical power, and a third mode in which the light source is turned off. As previously discussed, the compartment 60 can further include the electronics or printed circuit board assembly (PCBA) 55, which can operate the light source (e.g., provide the required current and voltage that causes the light source to emit light at different power levels).

Figure 6:
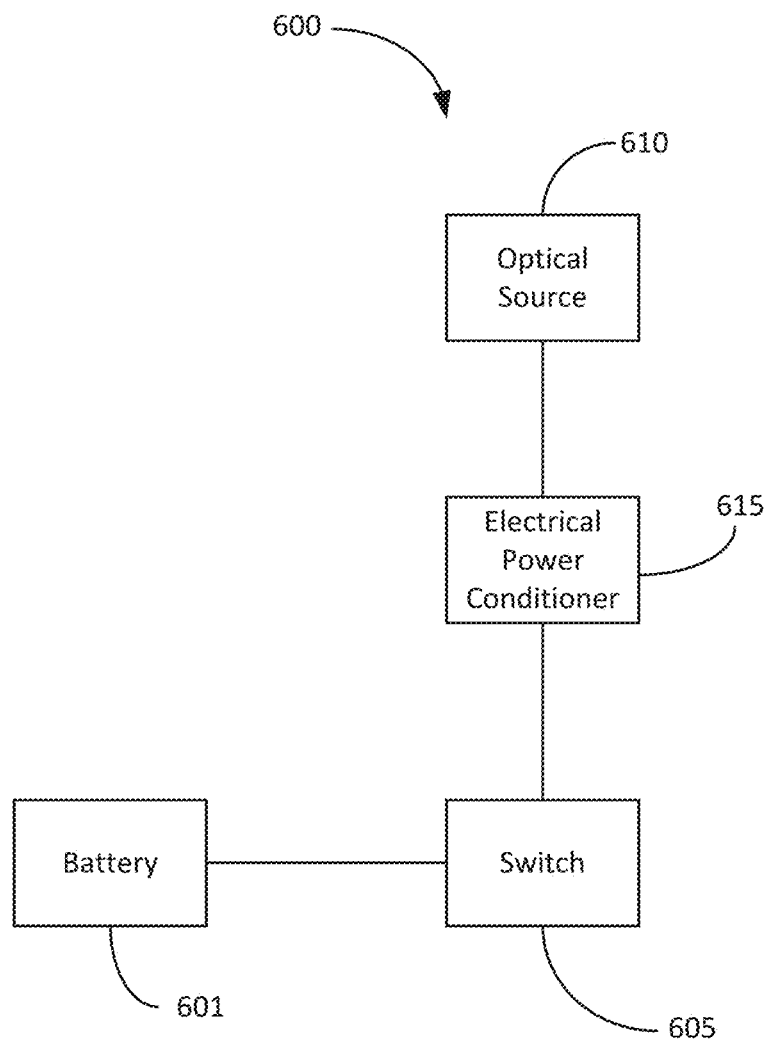
FIG. 6 schematically illustrates a system configured to provide electrical power to a light source of the endoscope.

FIG. 6 shows a schematic of a system 600 configured to provide electrical power to the light source. The system 600 can be implemented on the printed circuit board assembly (PCBA) 55 for use with the endoscope 100. The system 600 can condition the output of one or more single use batteries 40 to cause the light source (represented by an block 610) to emit light. In the system 600, the one or more single use batteries 40 is represented by reference numeral 601 and the electronic switch is represented by reference numeral 605. The electronic switch 605 electrically connects the one or more single use batteries 601 to the light source 610 via an electric power conditioner 615. The electronic power conditioner is configured to provide a required electrical current and/or voltage that causes the light source to output different amounts of light output. In one implementation, the electronic switch can be an infinitely variable switch adjustable by a user. In another implementation, the electronic switch can operate between a plurality of different modes (e.g., three modes). In a first mode, the electric power conditioner 615 upconverts the voltage output from the one or more single use batteries 601 to a first voltage required to cause the light source 610 to emit light at a first optical power. In a second mode, the electric power conditioner 615 upconverts the voltage output from the one or more single use batteries 601 to a second voltage required to cause the light source 610 to emit light at a second optical power. In a third mode, the electric power conditioner 615 terminates electrical power supplied to the light source 610 such that it turns off. In some implementations, the electric power conditioner 615 is configured to terminate electrical power supplied to the light source 610 if the voltage output from the one or more single use batteries 601 is below a threshold voltage (e.g., a threshold voltage of about 1.25 Volts). In some implementations, the one or more single use batteries 601 can power the light source for about four (4) hours. For example, the one or more single use batteries can have sufficient energy to cause the light source to output the maximum rated optical power continuously for about four (4) hours. Various implementations of the battery powered endoscopes 100 described above can be disposed of (e.g., thrown out) once the voltage output from the one or more single use batteries 601 is below a threshold voltage (e.g., a threshold voltage of about 1.25 Volts). Accordingly, various implementations of the battery powered endoscopes 100 described above can be single use endoscopes that are not capable of being reused.

Figure 7:
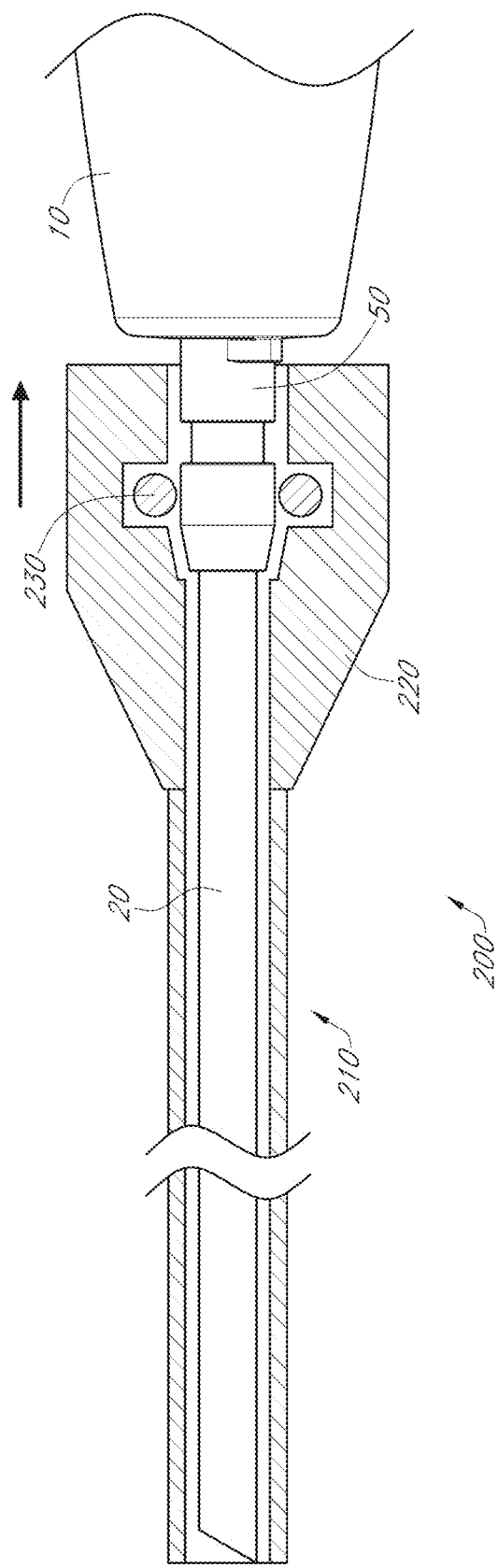
FIG. 7 is a schematic cross-sectional side view of an endoscope coupled to a cannula.

FIG. 7 shows a cannula 200 having a cannula tube 210 and a cannula connector 220 slid over the endoscope tube 20 and connector 50 during a coupling operation of the cannula 200 to the endoscope 100. The cannula connector 220 can have one or more seals 230 that can lockingly engage the recessed or circumferential groove or slot 52 of the connector 50 once the cannula connector 220 is fully coupled with the connector 50. Optionally, the connector 50 can have a key portion, such as the key portion 59 (see FIGS. 1C), to register and couple with the cannula 200 in a particular rotational orientation. Optionally, the cannula connector 220 engages the connector 50 so that a proximal surface of the connector 220 is adjacent (e.g., in contact with) a distal surface of the housing 10. For simplicity, only a distal portion of the housing 10 is shown. However, one skilled in the art will recognize that the rest of the housing 10 in FIG. 7 may or may not be similar to the housing 10 shown in FIG. 1A-2.

Figure 9:
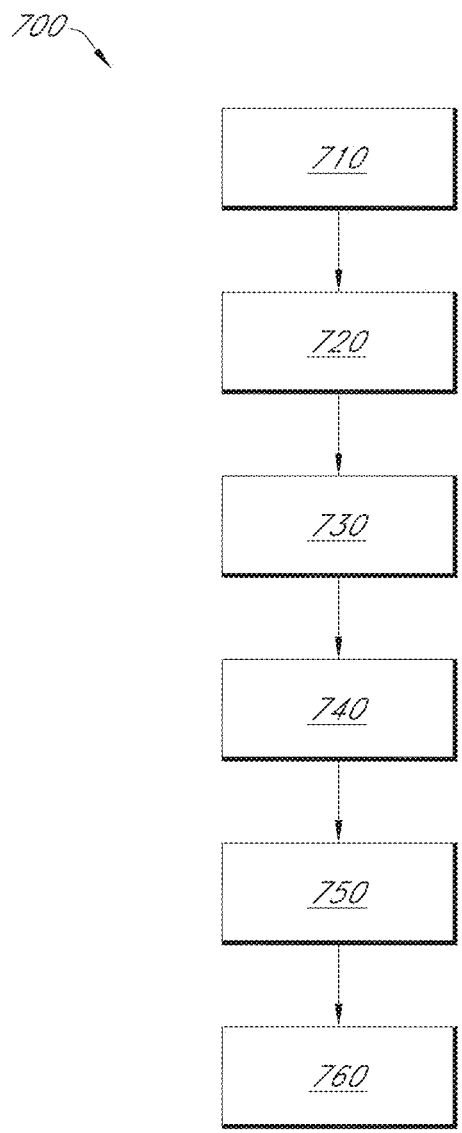
FIG. 9 is a flowchart illustrating a method of using the endoscope in an arthroscopic procedure.

FIG. 8 is a schematic view of the endoscope 100 inserted into a cannula 200 positioned in a knee joint K during a knee arthroscopic procedure, and the camera 300 attached to the endoscope 100 as described above. FIG. 9 is a flowchart illustrating a method 700 of using the endoscope 100 (e.g., in an arthroscopic procedure). Prior to use, the endoscope 100 can be sterilized 710, as described above. In one implementation, an incision is made 720 in the knee and the cannula inserted 730 through the incision to the surgical site. The endoscope 100 is then inserted 740 into the cannula so that the cannula connector 220 couples to the connector 50. The camera 300 is then coupled 750 to the eyepiece 30. As discussed above, the surgeon can easily rotate the endoscope 100 to alter the view provided of the surgical site (e.g. to provide a different angular view). In one implementation, as discussed above, the endoscope 100 can operate for a period of between about 2 hours and about 5 hours, such as about 3-4 hours, for example about 4 hours. Once use of the endoscope 100 is completed (e.g., once the surgical procedure is completed), the endoscope 100 can be disposed of 760.

Additional Embodiments

In embodiments of the present invention, an endoscope system may be in accordance with any of the following clauses:

Clause 1: A cordless endoscope assembly, comprising:
a housing that defines an ergonomic handpiece sized to be held between a palm and one or more fingers of a user's hand;
an endoscope tube that extends distally of the housing;
an eyepiece that extends proximally of the housing; and
electronics housed in the housing and configured to operate one or more light sources in the endoscope, the electronics comprising one or more batteries and a printed circuit board,
wherein the housing includes a connector configured to removably couple with a cannula connector of a cannula when the endoscope tube is inserted through the cannula.

Clause 2: The assembly of clause 1, wherein the housing comprises a front housing portion that removably couples to a rear housing portion to define the housing, the front housing portion defining the connector.

Clause 3: The assembly of any preceding clause, wherein the front housing portion is interchangeable between a plurality of front housing portions, each having a different connector configured to couple to one of a plurality of different cannulas.

Clause 4: The assembly of any preceding clause, wherein the endoscope is rotatable by a user via the handpiece about an axis of the endoscope tube.

Clause 5: The assembly of any preceding clause, wherein the eyepiece is configured to removably engage a coupling member of a camera.

Clause 6: The assembly of any preceding clause, wherein the housing, endoscope tube, electronics and eyepiece are disposable as an integral unit.

Clause 7: The assembly of any preceding clause, wherein the housing, endoscope tube, electronics and eyepiece are sterilizable as an integral unit.

Clause 8: The assembly of any preceding clause, wherein the connector comprises a locking groove or recess.

Clause 9: The assembly of any preceding clause, wherein the connector comprises a key member configured to engage the cannula in a particular orientation.

Clause 10: The assembly of any preceding clause, further comprising a switch interface on the housing actuatable by a user to operate a light source of the endoscope assembly.

Clause 11: The assembly of any preceding clause, wherein the one or more batteries include a AA alkaline battery.

Clause 12: The assembly of any preceding clause, wherein the one or more batteries comprise a flat button cell.

Clause 13: The assembly of any preceding clause, wherein the endoscope assembly is configured for sterilization using an ethylene oxide (EtO) sterilization process.

Clause 14: A cordless endoscope kit, comprising:
a rear housing portion;
a plurality of front housing portions, each front housing portion coupleable to the rear housing portion to define a housing and ergonomic handpiece, each of the front housing portions having a different connector, each connector configured to couple to one of a plurality of different cannulas;
an endoscope tube that extends distally of the front housing portion;
an eyepiece coupled to the rear housing portion; and electronics housed in a cavity of the housing and configured to operate one or more light sources in the endoscope, the electronics comprising one or more batteries and a printed circuit board.

Clause 15: The kit of clause 14, wherein the housing, endoscope tube, electronics and eyepiece are disposable as an integral unit.

Clause 16: The kit of any of clauses 14-15, further comprising a switch interface on the housing actuatable by a user to operate a light source of the endoscope assembly.

Clause 17: The kit of any of clauses 14-16, wherein the one or more batteries include a AA alkaline battery.

Clause 18: The kit of any of clauses 14-17, wherein the one or more batteries comprise a flat button cell.

Clause 19: The kit of any of clauses 14-18, wherein the endoscope assembly is configured for sterilization using an ethylene oxide (EtO) sterilization process.

Clause 20: A method of manufacturing a cordless endoscope, comprising:

forming or providing a rear housing portion;

forming or providing a plurality of front housing portions, each front housing portion coupleable to the rear housing portion to define a housing and ergonomic handpiece, each of the front housing portions having a different connector, each connector configured to couple to one of a plurality of different cannulas;

selecting one of the plurality of front housing portions;

disposing in a compartment between said one of the plurality of front housing portions and the rear housing portion electronics configured to operate one or more light sources in the endoscope, the electronics comprising a battery and a printed circuit board assembly (PCBA); and coupling said one of the plurality of front housing portions to the rear housing portion to assemble the endoscope, an endoscope tube extending distally of the front housing portion and an eyepiece coupled to the rear housing portion, wherein the assembled endoscope is disposable as a single unit.

While certain embodiments of the invention have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A cordless endoscope, comprising:
   a cordless housing that defines an ergonomic handpiece sized to be held between a palm and one or more fingers of a user's hand, the housing having a front housing portion that removably couples to a rear housing portion along respective edges of the front housing portion and the rear housing portion to define the cordless housing;
   an endoscope tube that extends distally of the front housing, the endoscope tube linearly extending to a distal end about an axis transverse to the ergonomic handpiece;
   an eyepiece that extends proximally of the housing; and
   electronics housed in a compartment of the cordless housing, a first part of the compartment defined within the front housing portion and a second part of the compartment defined within the rear housing portion, the electronics configured to operate one or more light sources in the cordless endoscope, the electronics comprising one or more batteries and a printed circuit board, the electronics extending within the first part of the compartment and the second part of the compartment,
   wherein the front housing portion is formed with a connector configured to removably couple with a cannula connector of a cannula when the endoscope tube is inserted through the cannula, the front housing portion formed with the connector at a distal end of the front housing portion, and wherein the cordless endoscope is rotatable about the axis of the endoscope tube.

2. The cordless endoscope of claim 1, wherein the front housing portion is interchangeable between a plurality of front housing portions, each having a different shaped connector configured to couple to a correspondingly shaped connector on one of a plurality of different cannulas.

3. The cordless endoscope of claim 1, wherein the cordless endoscope is rotatable by a user via the handpiece.

4. The cordless endoscope of claim 1, wherein the eyepiece is configured to removably engage a coupling member of a camera.

5. The cordless endoscope of claim 1, wherein the housing, endoscope tube, electronics and eyepiece are disposable as an integral unit.

6. The cordless endoscope of claim 1, wherein the housing, endoscope tube, electronics and eyepiece are sterilizable as an integral unit.

7. The cordless endoscope of claim 1, wherein the connector comprises a locking groove or recess.

8. The cordless endoscope of claim 1, wherein the connector comprises a locking member configured to engage the cannula in a particular rotational orientation.

9. The cordless endoscope of claim 1, further comprising a switch interface on the housing, the switch interface being actuatable by a user to operate the one or more light sources of the cordless endoscope.

10. The cordless endoscope of claim 1, wherein the one or more batteries include a AA alkaline battery.

11. The cordless endoscope of claim 1, wherein the one or more batteries comprise a flat button cell.

12. The cordless endoscope of claim 1, wherein the cordless endoscope is configured for sterilization using an ethylene oxide (EtO) sterilization process.

13. A kit for a cordless endoscope, comprising:
   a rear housing portion;
   a plurality of interchangeable front housing portions, each front housing portion coupleable to the rear housing portion along respective edges of the front housing portion and the rear housing portion to define a cordless housing and ergonomic handpiece, each of the front housing portions formed with a different shaped connector at a distal end of the front housing portion, each connector configured to couple to a correspondingly shaped cannula connector of one of a plurality of different cannulas;
   an endoscope tube that extends distally of the front housing portion and transverse to the ergonomic handpiece;
   an eyepiece coupled to the rear housing portion; and
   electronics housed in a cavity of the cordless housing, a first part of the cavity defined within the front housing portion and a second part of the cavity defined within the rear housing portion, the electronics configured to operate one or more light sources in the cordless endoscope, the electronics comprising one or more batteries and a printed circuit board, the electronics extending within the first part of the cavity and the second part of the cavity.

14. The kit of claim 13, wherein the housing, endoscope tube, electronics and eyepiece are disposable as an integral unit.

15. The kit of claim 13, further comprising a switch interface on the housing, the switch interface being actuatable by a user to operate the one or more light sources.

16. The kit of claim 13, wherein the one or more batteries include a AA alkaline battery.

17. The kit of claim 13, wherein the one or more batteries comprise a flat button cell.

18. The kit of claim 13, wherein the housing, endoscope tube, electronics and eyepiece are sterilizable as a single unit using an ethylene oxide (EtO) sterilization process.

19. A method of manufacturing a cordless endoscope, comprising:

forming or providing a rear housing portion;

forming or providing a plurality of interchangeable front housing portions, each front housing portion coupleable to the rear housing portion along respective edges of the front housing portion and the rear housing portion to define a cordless housing and ergonomic handpiece, each of the front housing portions formed with a different shaped connector at a distal end of the front housing, each connector configured to couple to a correspondingly shaped cannula connector one of a plurality of different cannulas;

selecting one of the plurality of front housing portions;

disposing electronics in a compartment of the cordless housing, a first part of the compartment defined within said one of the plurality of front housing portions and a second part of the compartment defined within the rear housing portion, the electronics configured to operate one or more light sources in the cordless endoscope, the electronics comprising a battery and a printed circuit board assembly (PCBA), the electronics extending within the first part of the compartment and the second part of the compartment; and coupling said one of the plurality of front housing portions to the rear housing portion to assemble the endoscope, an endoscope tube extending distally of the front housing portion and transverse to the ergonomic handpiece, and an eyepiece coupled to the rear housing portion, wherein the assembled cordless endoscope is disposable as a single unit.

* * * * *